United States Patent [19]
Sievers et al.

[11] Patent Number: 5,301,664
[45] Date of Patent: Apr. 12, 1994

[54] METHODS AND APPARATUS FOR DRUG DELIVERY USING SUPERCRITICAL SOLUTIONS

[76] Inventors: Robert E. Sievers, 655 Northstar Ct., Boulder, Colo. 80304; Brooks M. Hybertson, 280 County Rd. 83; Brian N. Hansen, 1510 Eisenhower Dr., both of Boulder, Colo. 80302

[21] Appl. No.: 846,331

[22] Filed: Mar. 6, 1992

[51] Int. Cl.$^5$ .................... A61M 15/00; B65D 37/00
[52] U.S. Cl. .................... 128/200.23; 128/203.15; 222/207
[58] Field of Search .................... 222/625, 207; 128/203.15, 200.24, 200.23, 203.12, 203.23, 202.21; 424/DIG. 1

[56] References Cited

U.S. PATENT DOCUMENTS

| | | | |
|---|---|---|---|
| 3,856,185 | 12/1974 | Riccio | 222/635 |
| 4,044,126 | 8/1977 | Cook et al. | 514/180 |
| 4,066,596 | 1/1978 | Stern | 222/635 |
| 4,206,758 | 6/1980 | Hallworth et al. | 128/203.15 |
| 4,353,365 | 10/1982 | Hallworth et al. | 128/203.15 |
| 4,364,923 | 12/1982 | Cook et al. | 424/46 |
| 4,414,209 | 11/1983 | Cook et al. | 514/180 |
| 4,582,731 | 4/1986 | Smith | 427/421 |
| 4,627,432 | 12/1986 | Newell et al. | 128/203.15 |
| 4,800,903 | 1/1989 | Ray | 128/202.21 X |
| 4,811,731 | 3/1989 | Newell et al. | 128/203.15 |
| 4,892,232 | 1/1990 | Martin | 222/207 |
| 4,963,367 | 10/1990 | Ecanow | 424/485 |
| 4,970,093 | 11/1990 | Sievers et al. | 427/38 |
| 5,002,048 | 3/1991 | Makiej, Jr. | 128/200.23 |
| 5,013,720 | 5/1991 | Whitsett | 514/12 |
| 5,044,523 | 9/1991 | McNab | 222/207 |
| 5,056,511 | 10/1991 | Ronge | 128/200.14 |
| 5,115,803 | 5/1992 | Sioutas | 128/200.23 |
| 5,126,126 | 6/1992 | Varaprath | 424/71 |
| 5,169,433 | 12/1992 | Lindsay | 71/118 |

FOREIGN PATENT DOCUMENTS

| | | | |
|---|---|---|---|
| 81014 | 6/1983 | European Pat. Off. | 222/635 |
| 2501644 | 9/1982 | France | 222/635 |
| 1577796 | 7/1990 | U.S.S.R. | 128/203.15 |
| 1591990 | 9/1990 | U.S.S.R. | 128/203.15 |
| 9007351 | 7/1990 | World Int. Prop. O. | 128/203.15 |
| 9015635 | 12/1990 | World Int. Prop. O. | 128/203.15 |

OTHER PUBLICATIONS

"Solids Formation After The Expansion of Supercritical Mixtures", Rahoma S. Mohamed et al., *Supercritical Fluid Science & Technology*, ACS, 1989.
Condensed Chemical Dictionary, 10th Edition, p. 450 Van Nostrand Reinhold Co, 1982.

*Primary Examiner*—Edgar S. Burr
*Assistant Examiner*—Eric P. Raciti
*Attorney, Agent, or Firm*—Lowe, Price, LeBlanc & Becker

[57] ABSTRACT

Methods and apparatus for delivering physiologically active compounds to a target human or animal employ a supercritical fluid solution comprising a supercritical fluid solvent and a physiologically active solute. The supercritical fluid solution is passed into a subcritical region to evaporate the solvent and form a gas-borne dispersion of solute particles. The gas-borne dispersion of solute particles is administered directly to the target human or animal. The apparatus for delivering the physiologically active compound are of the hand-held type.

21 Claims, 2 Drawing Sheets

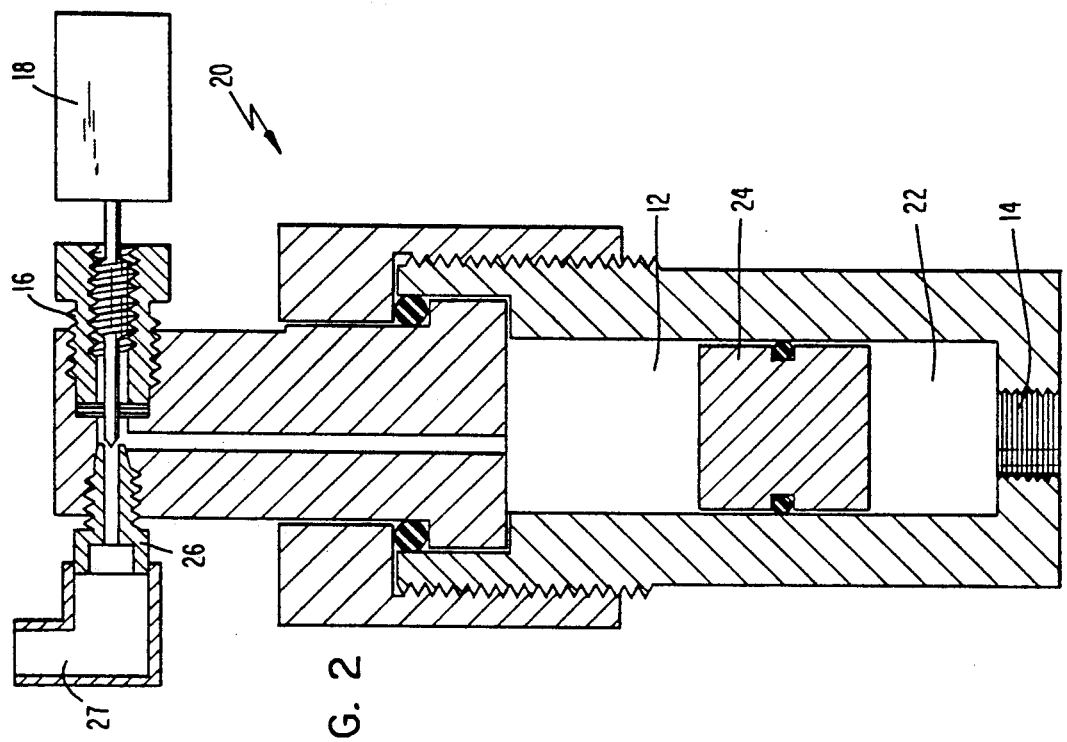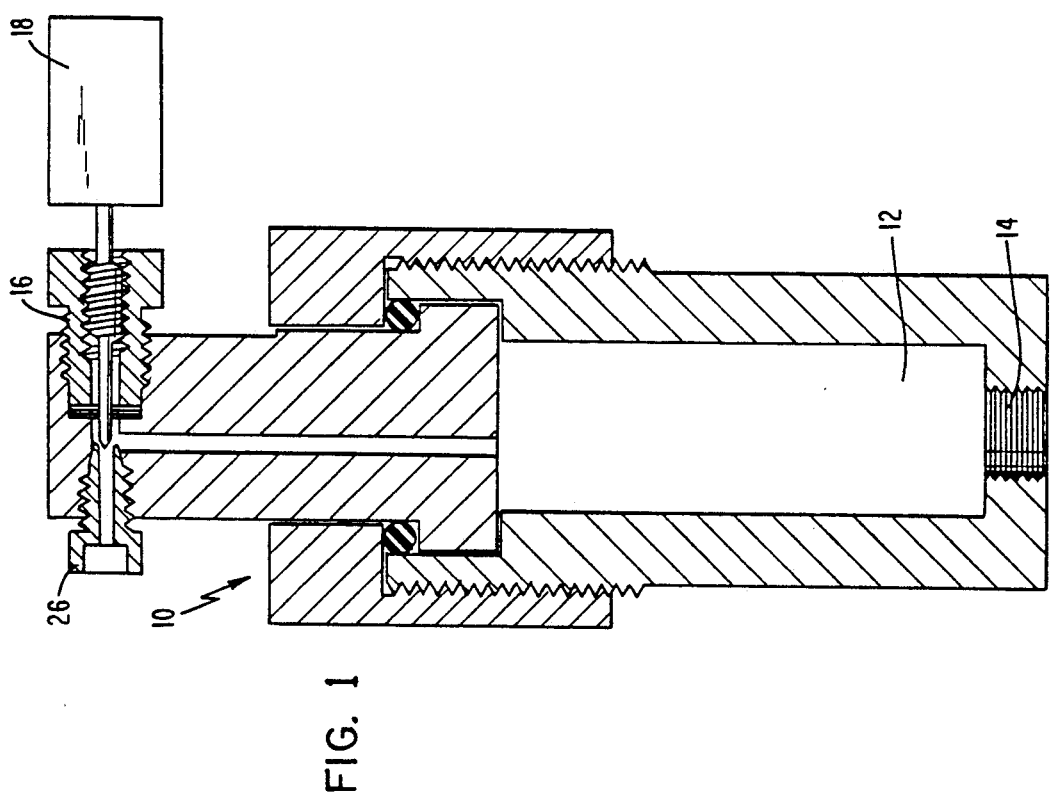

METHODS AND APPARATUS FOR DRUG DELIVERY USING SUPERCRITICAL SOLUTIONS

FIELD OF THE INVENTION

The present invention relates to methods and apparatus for delivering a physiologically active compound to a target human or animal. More particularly, the present invention relates to methods and apparatus for delivering physiologically active compounds to a target human or animal using supercritical fluid solutions comprising a supercritical fluid solvent and a physiologically active solute.

BACKGROUND OF THE INVENTION

Various methods of drug administration are known in the art, including hypodermic delivery, oral delivery and nasal delivery. Hypodermic delivery of drugs is disadvantageous in that it can cause localized damage to arteries from repeated injections, create highly concentrated doses of drugs in tissues before the drugs are distributed by the circulatory system, and increase the probability of infection from hypodermic use. Oral administration of drugs is advantageous in patient convenience, and therefore increases the probability of patient compliance. Nasal and pulmonary drug delivery methods and apparatus are advantageous owing to low patient discomfort, rapid drug absorption, reduced degradation of drug compounds by the gastrointestinal system and reduced systemic side effects resulting from the drugs.

Conventional oral and nasal drug delivery methods and apparatus often employ aerosol formulations. For example, the Cook et al U.S. Pat. Nos. 4,044,126, 4,414,209 and 4,364,923 relate to the use of aerosol formulations for the adminstration of anti-inflammatory steroids. The Cook et al patents disclose a method for preparing the steroid in a crystalline form for use in the aerosol formulations. The Tom et al publication entitled "Particle Formation with Supercritical Fluids-A Review", *Journal of Aerosol Science*, Volume 22, No. 5, pages 555–584 (1991), discloses the use of supercritical solutions to form particles for use in aerosol formulations. The Smith U.S. Pat. No. 4,582,731 and the Sievers et al U.S. Pat. No. 4,970,093 further disclose the use of supercritical fluids for powder and film formation, but do not relate particularly to powders or films of medicaments or drugs. The use of supercritical fluid solutions to form precipitates of various metal salts was first disclosed by Hannay et al, *Chem. News*, 40,256 (1879).

It is also known to administer powdered medicaments orally or nasally. The Hallworth et al U.S. Pat. Nos. 4,206,758 and 4,353,365 disclose inhalation devices by which powdered medicaments can be orally or nasally inhaled by a patient through a nozzle. The Newell et al U.S. Pat. Nos. 4,627,432 and 4,811,731 disclose additional inhalation devices for administering medicaments in finely divided solid form or in fluid form.

Owing to the advantages of oral and nasal drug delivery as discussed above, a continuing need exists for additional methods and apparatus for successful oral and nasal drug delivery.

SUMMARY OF THE INVENTION

Accordingly, it is an object of the present invention to provide methods and apparatus for delivering a physiologically active compound to a target human or animal. It is a further object of the present invention to provide methods and apparatus for oral or nasal delivery of the physiologically active compound to the target human or animal. It is a further object of the invention to provide methods and apparatus for delivering a physiologically active compound to a target human or animal wherein the amount of active compound which reaches the desired target area is increased as compared with conventional methods and apparatus. It is an additional object of the present invention to form solute particles of a size which is optimal for inhalation and retention, preferably of from 0.5 μm to about 6.5 μm.

These and additional objects are provided by the methods and apparatus of the present invention. In accordance with the methods of the present invention, a physiologically active compound is delivered to a target human or animal by forming a supercritical fluid solution comprising a supercritical fluid solvent and a physiologically active solute, passing the solution into a subcritical region to evaporate or vaporize the solvent and form a gas-borne dispersion of solute particles, and administering the gas-borne dispersion of solute particles to the target human or animal. Applicants have discovered that the gas-borne dispersion of solute particles which is formed by passing the supercritical solution into a subcritical region is advantageous for direct administration to a target human or animal.

The apparatus according to the present invention are of the hand-held type, thereby affording convenient individual use. In one embodiment, the apparatus comprises a first chamber containing a supercritical fluid solution comprising a supercritical fluid solvent and a physiologically active solute, and means for rapidly expanding the solution into a subcritical region to evaporate or vaporize the solvent and form a gas-borne dispersion of solute particles. In a second embodiment, the hand-held apparatus comprises a first chamber containing a supercritical fluid solvent, a second chamber containing a physiologically active solute for the solvent, means for passing the solvent from the first chamber into the second chamber to solubilize the solute in the solvent and form a supercritical fluid solution, and means for rapidly expanding the solution into a subcritical region to evaporate the solvent and form a gas-borne dispersion of solute particles.

The present methods and apparatus are advantageous in that the gas-borne dispersion of solute particles is suitable for direct oral or nasal administration to a human or animal. The methods and apparatus allow the production of extremely small sized particles, less than about 6.5 μm in diameter, and in many cases less than about 1 μm in diameter, whereby the amount of active compound which is delivered to the target area of the human or animal is significantly increased over conventional methods and apparatus.

These and additional objects and advantage will be more fully apparent in view of the following detailed description.

BRIEF DESCRIPTION OF THE DRAWING

The following detailed description will be more fully understood in view of the drawing in which:

FIG. 1 sets forth a first embodiment of the apparatus according to the present invention;

FIG. 2 sets forth a second embodiment of the apparatus according to the present invention;

FIG. 3 sets forth a third embodiment of the apparatus according to the present invention; and FIG. 4 sets forth an embodiment of the active compound-containing chamber of the apparatus set forth in FIG. 3.

DETAILED DESCRIPTION

Figure 4:
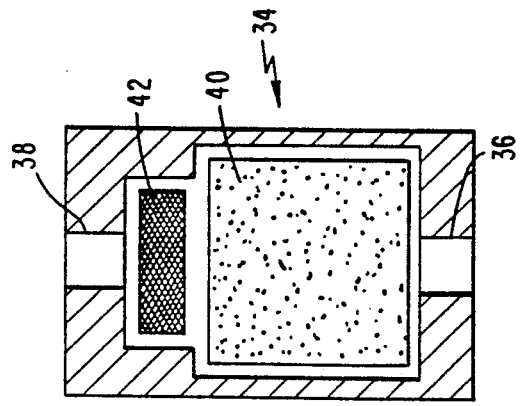

In accordance with the present methods for delivering a physiologically active compound to a target human or animal, a supercritical fluid solution is formed from the supercritical fluid solvent and a physiologically active solute. The solution is then passed into a subcritical region to evaporate the solvent and form a gas-borne dispersion of solute particles. The gas-borne dispersion of the solute particles is administered directly to a target human or animal.

As the supercritical fluid solution passes into the subcritical region, a rapid decompression occurs, resulting in a rapid loss of solvent strength (in less than about $10^{-6}$ sec) and a rapid precipitation of the active compound into fine particles. The speed of the solution decompression may be controlled to produce solute particles having an average particle size of less than about 6.5 μm in diameter, and in many cases down to about 0.5 μm in diameter. The gas-borne dispersion of solute particles, surprisingly contains a quantity of the active compound sufficient to provide an inhalation therapeutic dosage. The gas-borne dispersion of solute particles may be administered through the mouth or the nasal passages of the target human or animal. The gas-borne dispersion of solute particles may optionally be mixed with one or more additional gases, if desired, before administering to the target human or animal. For example, the gas-borne dispersion of solute particles may be mixed with oxygen or humidified air. Thus, the methods according to the present invention are advantageous for delivering various physiologically active compounds to a target human or animal.

Depending on the nature of the physiologically active solute, the rapid expansion of the supercritical solution may result in the formation of a gas-borne dispersion of solute vapor, and such methods are also within the scope of the present invention. An example of such a solute is camphor.

Within the context of the present invention, reference to the supercritical fluid solution indicates that the solution is above its critical pressure and temperature or is sufficiently close to the critical pressure and temperature to cause the formation of a gas-borne dispersion of solute particles of an average size of from about 0.5 μm to about 6.5 μm in diameter upon rapid expansion of the solution into a subcritical region.

In one embodiment, the supercritical fluid solution may be formed by mixing the supercritical fluid solvent and the physiologically active solute, pressurizing the resulting mixture above the critical pressure of the solvent, and heating the resulting mixture above the critical temperature of the solvent. Alternatively, the supercritical fluid solution may be formed by pressurizing the solvent above its critical pressure and heating the solvent above its critical temperature, and then mixing the pressurized, heated solvent with the physiologically active solute.

Various supercritical fluid solvents may be used in the methods of the present invention. An important feature in selecting a specific supercritical fluid solvent is to ensure that the physiologically active compound which is to be employed is soluble in the supercritical fluid solvent. Suitable supercritical fluid solvents include, but are not limited to, carbon dioxide, nitrous oxide, chlorofluorocarbons, for example, dicholorodifluoromethane, trichlorofluoromethane, and chlorodifluoromethane, xenon, sulfur hexafluoride, ethanol, acetone, propane, water, and mixtures thereof. Mixtures of two or more of these solvents may be particularly appropriate to increase the solubility of a particular physiologically active compound therein. In a preferred embodiment, the supercritical fluid solvent comprises carbon dioxide owing to its relatively low critical pressure and temperature (1072 psi; 31° C., respectively), low chemical reactivity, physiological safety, and relatively low cost.

Additionally, the solubility of many physiologically active compounds in a supercritical fluid solvent such as carbon dioxide may be improved by adding a small amount, for example up to several weight percent based on the weight of the solvent, of a polar modifier such as ethanol. In some instances, particularly for hydrophilic active compounds, it may be preferable to form reverse micelles of the polar active compounds suspended in the non-polar supercritical fluid solvent, for example, carbon dioxide or propane. The supercritical fluid solutions may further contain a surfactant, for example, a fatty acid, Tween ® 85, Tween ® 80, or dipalmitoylphosphatidyl choline. Such a surfactant may facilitate reverse micelle formation and allow solutions of such polar species as enzymes to be formed. In this regard, it will be apparent that the surfactant may serve as the physiologically active compound, for example in the treatment of various pulmonary disorders.

Various physiologically active compounds may be employed as the solute in the delivery methods of the present invention. Suitable physiologically active compounds include, but are not limited to anti-inflammatory agents, antibiotics, anti-viral agents, anti-neoplastic agents, antihistamines, peptides and proteins such as insulin. Suitable anti-inflammatory agents, including steroids, for use in the methods of the present invention include, but are not limited to, beclomethasone dipropionate, prednisone, flunisolone, dexamethasone, prednisolone, cortisone, theophylline, albuterol, cromolyn sodium, epinephrine, flunisolide, terbutaline sulfate, alpha-tocopherol (Vitamin E), dipalmitoylphosphatidylcholine, salmeterol and fluticasone propionate.

Examples of antibiotics that may be employed as the physiologically active solute in the methods of the present invention, include, but are not limited to tetracycline, choramphenicol, aminoglycosides, for example, tobramycin, beta-lactams, for example ampicillin, cephalosporins, erythromycin and derivatives thereof, clindamycin, and the like. Suitable anti-viral agents include acyclovir, ribavirin, ganciclovir and foscarnet. Suitable anti-neoplastic agents include, but are not limited to etoposid, taxol, and cisplatin. Antihistamines include, but are not limited to, diphenhydramine and ranitadine. These specific physiologically active compounds are only examples of the numerous active compounds which may be employed in the methods of the present invention.

In a preferred embodiment of the present methods, the physiologically active solute is a drug for the treatment of a pulmonary disorder. In this regard, preferred active compounds are selected from the group consisting of beclomethasone dipropionate, albuterol, cromolyn sodium, flunisolide, terbutaline sulfate, salmeterol and fluticasone dipropionate.

Thus, the present invention employs compositions comprising a supercritical fluid solvent and a physiologically solute, the solute being included in an amount sufficient to induce a physiological response when the composition is rapidly expanded into a subcritical region and administered to a target human or animal.

The present invention also relates to apparatus particularly adapted for use in connection with the described methods of delivering a physiologically active compound to a target human or animal. The apparatus of the invention are of the hand-held type and therefore are convenient for individual use. A first embodiment of an apparatus according to the invention comprises a chamber containing a supercritical fluid solution as described above comprising a supercritical fluid solvent and a physiologically active solute, and means for rapidly expanding the solution into a subcritical region to evaporate the solvent and form a gas-borne dispersion of solute particles.

An example of such an apparatus according to the invention is set forth in FIG. 1. With reference to FIG. 1, the hand-held apparatus 10 includes a chamber 12 containing the supercritical fluid solution. The chamber 12 includes inlet 14 for pressurized components. The chamber may be formed of any suitable, high strength material, preferably metal. The means for rapidly expanding the supercritical fluid solution into a subcritical region may comprise any expansion valve or restrictor device as is known in the art. In the apparatus 10 of FIG. 1, the rapid expansion means comprises an expansion valve assembly 16 operated by handle 18. As will be apparent, various expansion valves or restrictors may be employed, including, but not limited to, needle valves, ball valves, diaphragm valves, a fixed restricter such as a pinched tube or a closed tube partially reopened by grinding, frits and other porous materials.

A second embodiment of a hand-held apparatus according to the present invention is set forth in FIG. 2. With reference to FIGS. 1 and 2, like parts are identified by the same reference numeral in FIG. 2 as in FIG. 1. Thus, the hand-held apparatus 20 of FIG. 2 includes a chamber 12 including a pressurized component inlet 14 and an expansion valve assembly 16 operated by handle 18. The apparatus 20 set forth in FIG. 2 includes a second chamber 22 which contains a pressurized ballast fluid. The hand-held apparatus of this embodiment further includes an impermeable pressure sensitive barrier means arranged between the first chamber 12 and the second chamber 22 wherein the pressure sensitive barrier means allows the pressure of the ballast fluid to maintain the supercritical condition of the supercritical fluid solution as the solution passes through the rapid expansion means. With reference to FIG. 2, the impermeable pressure sensitive barrier means set forth therein comprises a sliding piston 24. As will be apparent, small changes in the supercritical fluid solution pressure during discharge through the rapid expansion means may substantially affect the solubility of the active compound and the size of the solute particles which are formed. Reducing the solubility of the active compound at or near saturation conditions can cause premature precipitation, thereby reducing the amount of active compound delivered and/or obstructing the discharge apparatus. Additionally, changing the solute particle size during delivery can cause undesirable modifications in the distribution of the gas-borne dispersion of solute particles.

While the apparatus of FIG. 2 includes a floating piston 24 as the impermeable pressure-sensitive barrier means, it will be apparent that other means may be employed. For example, the barrier means may comprise a flexible wall formed, for example of a collapsible bag, collapsible balloon or a collapsible bellows. Alternatively, a specific barrier means is not included in the apparatus but the difference in the densities or meniscus of the supercritical fluid solution and the ballast fluid is sufficiently large that the solution and the ballast fluid are separated from one another and are not intermixed.

The specific ballast fluid which is employed is not critical, as long as the ballast fluid exerts a pressure which maintains the supercritical condition of the solution as the solution passes through the rapid expansion means. Ideally, the ballast fluid comprises a gas in equilibrium with a liquid which has a vapor pressure equal to or greater than the critical pressure of the supercritical fluid solution.

The hand-held apparatus according to the present invention may further include means for administering the gas-borne dispersion of solute particles to a target human or animal. The administration means may include a mouthpiece, face mask or the like, as indicated by mouthpiece 26 in FIG. 1. In another embodiment, the administration means may comprise a tube, shown in cross-section by reference numeral 27 in FIG. 2, which is open at both ends and adapted for mounting at the expansion valve outlet or mouthpiece. The tube will allow one to draw ambient air in with the gas-borne dispersion and/or remove solvent on the inner surface of the tube, as will be explained in greater detail below.

Figure 3:
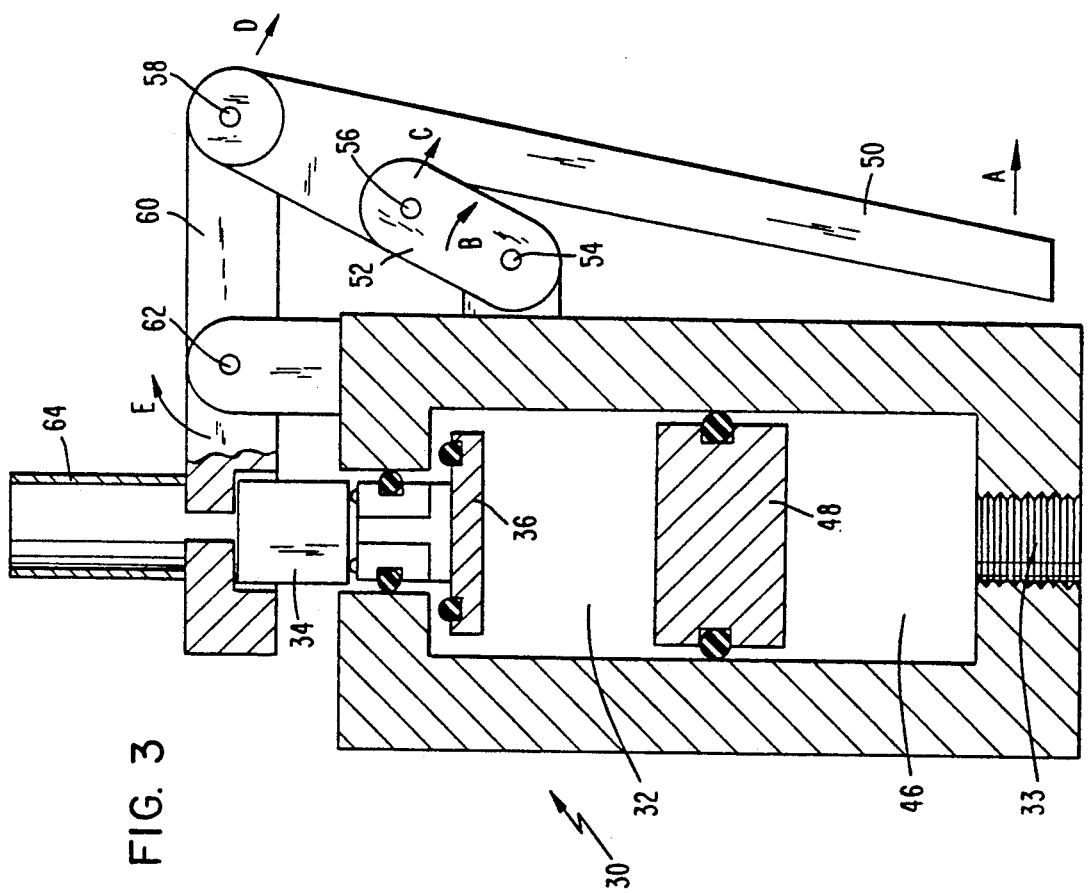

A further embodiment of the hand-held apparatus according to the present invention is set forth in FIGS. 3 and 4. In this embodiment, the apparatus comprises a first chamber containing a supercritical solvent, a second chamber containing the physiologically active solute for the solvent, and means for passing the solvent from the first chamber into the second chamber to solubilize the solute in the solvent and form a supercritical fluid solution. The apparatus further includes means for rapidly expanding the solution into a subcritical region to evaporate the solvent and form a gas-borne dispersion of solute particles. This embodiment of the apparatus is advantageous in that the active compound may be solubilized in the solvent immediately prior to or during delivery. Additionally, the second chamber containing the active solute may be replaceable and disposable. Thus, different active compounds may be used with the same apparatus and refill of the apparatus is facilitated.

FIG. 3 sets forth such a hand-held apparatus indicated generally by reference numeral 30. The apparatus includes a first chamber 32 containing a supercritical fluid solvent and a second chamber 34 containing a physiologically active solute for the solvent. An inlet 33 is included in the apparatus for supplying the pressurized contents. A pressure activated valve means 36 separates the first and second chambers and, when open, as shown in FIG. 3, allows passage of the solvent from the first chamber into the second chamber to solubilize the solute in the solvent and form the supercritical fluid solution.

FIG. 4 sets forth an enlarged view of one embodiment of the second chamber containing the active solute. With reference to FIG. 4, the chamber 34 is provided with a solvent inlet 36 and a solution outlet 38. The chamber 34 contains a removable support matrix 40 formed of a porous material having a high surface area, onto which the physiologically active solute has been deposited. In one embodiment, the active compound can be deposited on the matrix material by first dissolving the active compound in a supercritical fluid and contacting the resulting solution with the matrix material in a pressurized chamber. When the pressure is rapidly reduced, the active compound deposits in fine particles on the matrix and will be rapidly solubilized when contacted with the supercritical fluid solvent in the present apparatus. Other methods known in the art for depositing the active compound on a matrix may also be employed.

In the embodiment of FIG. 4, the means for rapidly expanding the resulting supercritical fluid solution into a subcritical region comprises a restrictor 423 formed of a frit material. As will be apparent, any type of restricter or rapid expansion means may be employed to rapidly expand the solution into a subcritical region to evaporate the solvent and form the gas-borne dispersion of the solute particles.

The hand-held apparatus of FIG. 3 includes an additional chamber 46 for containing a ballast fluid and pressure sensitive barrier means in the form of a movable piston 48 for maintaining the supercritical condition of the solvent, and later the solution, as the solvent passes through the chamber 34 and the solution passes through the rapid expansion means 42, in the manner described above with reference to FIG. 2. As will be apparent, the hand-held apparatus of FIG. 3 may be constructed without the additional chamber 46 and the pressure sensitive barrier means 48.

Delivery of the active compound from the hand-held apparatus set forth in FIG. 3 is effected with the dispensing lever 50 in the position shown. To discontinue delivery, the lever 50 is moved away from the apparatus in the direction of arrow A. This causes movement of a link 52 around a fixed pivot 54 in the direction of arrow B and movement of movable pivots 56 and 58 in the direction of arrows C and D, respectively. This results in rotation of pressure arm 60 around the fixed pivot 62 in the direction of arrow E to release the downward, valve-opening pressure on the chamber 34 and, in turn, the valve means 36, thereby closing the valve means 36.

As shown in FIG. 3, the hand-held apparatus may further include means for administering or guiding the gas-borne dispersion of solute particles to a target human or animal, for example in the form of a tube 64.

In a further embodiment, it may be desirable to remove any solvent which remains in the gas-borne dispersion of solute particles, whereby the interior surface of the tube walls may be provided with a semi-permeable membrane or reactive surface which removes solvent from the gas-borne dispersion of solute particles. Such a tube is similar to the denuder tubes that are often used by atmospheric chemists to pass particles straight through but selectively remove, and optionally replace, a specific gaseous species such as carbon dioxide. For example, humidified air or oxygen could replace the solvent in the gas-borne dispersion of solute particles.

The methods and apparatus according to the present invention are particularly advantageous in that they include the direct administration of the gas-borne dispersion of solute particles produced from the supercritical fluid solution to the target human or animal. Although supercritical fluid solutions have been suggested in the past as a means for producing particles, in the prior studies, the resulting particles were collected and further processed, for example, in aerosols, sprays, or films. Since the collection and further processing steps cause particles to agglomerate into larger particles which are unsuitable for inhalation, the methods and apparatus of the present invention provide significant advantages.

The following examples demonstrate specific embodiments of methods and apparatus according to the present invention.

EXAMPLE 1

This example employed a hand-held apparatus according to the present invention as shown in FIG. 2. With the expansion valve assembly removed and a floating piston at the bottom of the chamber cylinder, 8.0 grams of solid carbon dioxide and 0.1 gram of camphor, a safe model drug compound, was placed on top of the floating piston. The expansion valve assembly was threaded onto the cylinder body while the expansion valve was open. After the assembly was threaded tightly, the expansion valve was closed and the carbon dioxide was allowed to warm to room temperature. The pressurization valve inlet was then opened and the lower chamber was filled with a ballast fluid comprising nitrogen at a pressure of 2200 psig, thereby forcing the piston up the cylinder and compresses the camphor and carbon dioxide in the upper chamber above the supercritical pressure. The entire apparatus was heated to approximately 37° C., approximately human body temperature, and above the critical temperature of carbon dioxide (31° C.). The expansion valve was opened and a strong smell of camphor was observed. This example demonstrates the advantages of the present methods and apparatus in that they may be employed in remote locations, requiring no electricity, complex pumping systems or the like.

EXAMPLE 2

Alpha-tocopherol (Vitamin E) is a cellular antioxidant which protects lung tissue against damage by lipid peroxidation caused by inhalation of common environmental oxidant gases such as oxygen, ozone and nitrogen dioxide. In this example, alpha-tocopherol was delivered to male, Sprague-Hawley rats using the methods of the present invention. 200 mg of alpha-tocopherol was pressurized with 2800 psig of carbon dioxide and maintained at 35.0° C. The resultant supercritical fluid solution was decompressed through a 5.8 cm long, 25 $\mu$m I.D. restrictor nozzle. The resulting gas-borne dispersion of alpha-tocopherol particles and carbon dioxide gas was mixed with 6.0 l/min of oxygen and administered to the rats in a delivery chamber. The subject animals were gently restrained so that their noses were positioned inside the delivery chamber. After 10 min. of exposure, the rats were removed from the chamber, anesthetized, and their lungs were perfused and surgically removed. High pressure liquid chromatography (HPLC) measurements of alpha-tocopherol concentrations in solvent extracts of lung homogenates of the dosed animals were compared to samples from untreated, control animals. It was shown that the dosed animals had alpha-tocopherol levels per gram of lung tissue (wet) of 32.6 $\mu$g/g compared to 18.1 $\mu$g/g for the control animals, indicating a rapid and substantial dosing in the treated animals. A sample of the gas-borne dispersion of alpha-tocopherol particles was collected. The particles were verified to be of an easily respirable size, diameter approximately 1 to 3 $\mu$m, by scanning electron microscopy (SEM).

EXAMPLE 3

This example demonstrates a method according to the invention for delivering cholesterol, a model compound for the steroid class of compounds. Specifically, a supercritical solution of carbon dioxide and cholesterol was formed and then passed into a subcritical region in a manner similar to that described in Example 2. Resulting cholesterol particles from the gas-borne dispersion were collected in the subcritical region by impaction on a glass slide and on an aluminum scanning electron microscope (SEM) mount. Analysis of the collected particles by SEM indicated that the particle diameter was approximately 2-3 $\mu$m, a size significantly smaller than the starting material which was used to form the supercritical solution. This size is also significantly smaller than droplets commonly formed using conventional aerosol generation means.

EXAMPLE 4

In this example, a sample of an organic dye, Oil Blue N, was combined with carbon dioxide to form a supercritical fluid solution. The solution was passed through a restrictor nozzle having a length of 1 cm and an inside diameter of 25 $\mu$m. Particles from the resulting gas-borne dispersion of particles were collected and analyzed by SEM. The particles had diameters approximately from 0.3 $\mu$m to 1 $\mu$m, a size range which is easily respirable.

EXAMPLE 5

In a manner similar to that of Example 2, an ethanol solution of dipalmitoylphosphatidylcholine (DPPC) was dissolved in supercritical carbon dioxide. The resultant supercritical fluid solution was expanded through a restrictor into a region of room temperature and atmospheric pressure (630 Torr in Boulder, Colo.), and fine particles of the DPPC were collected in a small glass test tube. In this experiment the ethanol acted as a supercritical fluid solvent polarity modifier. Thin layer chromatography (TLC) was used with a sulfuric acid/molybdenum oxide developing solution (specific for phospholipids) to confirm that the collected particles contained the desired DPPC. This compound was chosen because it is the major constituent of natural lung surfactant. It is proposed that the gas-borne dispersion of DPPC may be efficacious in the treatment of respiratory distress syndrome (RDS), an illness which is marked by insufficient lung surfactant function. Other natural or synthetic surfactants, such as fatty acids, long chain alcohols, esters, or mixtures thereof, may also be employed in the present methods. Surfactants in such methods can serve as the physiologically active agent, as a solvent polarity modifier, as a micelle formation facilitator, or as any combination of these.

EXAMPLE 6

In a manner similar to that of Example 2, lazaroid compound U-74389F in ethanol was dissolved in supercritical carbon dioxide at 35° C. and 2800 psi. The resultant supercritical fluid solution was expanded through a nozzle into a region of room temperature and atmospheric pressure, and the U-74389F particles were collected in a glass tube filled with ethanol. The composition of the drug after expansion was verified by comparison of its UV-visible absorption spectrum with that of a standard in ethanol. Lazaroids are a class of compounds that are proposed to be used as therapeutic antioxidants for the treatment of a variety of oxygen radical mediated processes.

The preceding examples are set forth to illustrate specific embodiments of the invention and are not intended to limit the scope of the methods and apparatus of the present invention. Additional embodiments and advantages within the scope of the claimed invention will be apparent to one of ordinary skill in the art.

What is claimed:

1. A method of delivering a physiologically active compound to a target human or animal, comprising (a) forming a supercritical fluid solution comprising a supercritical fluid solvent and a physiologically active solute; (b) passing the supercritical fluid solution into a region in which the temperature and pressure of the solvent are below a critical temperature and a critical pressure, respectively, of the solvent to evaporate the solvent and form a gas-borne dispersion of solute particles; and (c) administering the gas-borne dispersion of solute particles to the target human or animal.

2. A method as defined by claim 1, wherein the supercritical fluid solution is formed by mixing the supercritical fluid solvent and the physiologically active solute, pressurizing the mixture above the critical pressure of the solvent and heating the mixture above the critical temperature of the solvent.

3. A method as defined by claim 1, wherein the supercritical fluid solution is formed by pressurizing the supercritical fluid solvent above its critical pressure, heating the solvent above its critical temperature, and mixing the pressurized, heated solvent with the physiologically active solute.

4. A method as defined by claim 1, wherein the supercritical fluid solvent is selected from the group consisting of carbon dioxide, nitrous oxide, a chlorofluorocarbon, and mixtures thereof.

5. A method as defined by claim 4, wherein the supercritical fluid solution further includes a cosolvent selected from the group consisting of methanol, ethanol, water and acetone.

6. A method as defined by claim 1, wherein the supercritical fluid solution further includes a surfactant.

7. A method as defined by claim 1, wherein the physiologically active solute is an orally or nasally administrable drug for the treatment of a pulmonary disorder.

8. A method as defined by claim 7, wherein the physiologically active solute is selected from the group consisting of beclomethasone dipropionate, albuterol, cromolyn sodium, flunisolide, terbutaline sulfate, salmeterol and fluticasone dipropionate.

9. A method as defined by claim 1, wherein the physiologically active solute is selected from the group consisting of an anti-inflammatory agent, an antibiotic, an anti-viral agent, an anti-neoplastic agent, an antihistamine, a peptide and a protein.

10. A method as defined by claim 1, wherein the physiologically active solute is a surfactant selected from the group consisting of dipalmitoylphosphatidyl choline and a fatty acid.

11. A method as defined by claim 1, wherein the solute particles contained in the gas-borne dispersion have an average size of from about 0.5 $\mu$m to about 6.5 $\mu$m in diameter.

12. A method as defined by claim 1, wherein the gas-borne dispersion of solute particles is administered to the nasal or oral passages of the target human or animal.

13. A hand-held apparatus for delivering a physiologically active compound to a target human or animal, comprising (a) a first chamber containing a supercritical fluid solution comprising a supercritical fluid solvent and a physiologically active solute; (b) means for rapidly expanding the solution into a region in which the temperature and pressure of the solvent are below a critical temperature and a critical pressure, respectively, of the solvent to evaporate the solvent and form a gas-borne dispersion of solute particles; and (c) means for guiding the gas-borne dispersion of solute particles to a target human or animal.

14. A hand-held apparatus as defined by claim 13, wherein the rapid expansion means comprises an expansion valve.

15. A hand-held apparatus as defined by claim 13, further including means for administering the gas-borne dispersion of solute particles to a target human or animal.

16. A hand-held apparatus for delivering a physiologically active compound to a target human or animal, comprising a first chamber containing a supercritical fluid solvent; a second chamber containing a physiologically active solute for the solvent; means for passing the solvent form the first chamber into the second chamber to solubilize the solute in the solvent and form a supercritical fluid solution; means for rapidly expanding the solution into a region in which the temperature and pressure of the solvent are below a critical temperature and a critical pressure, respectively, of the solvent to evaporate the solvent and form a gas-borne dispersion of solute particles; and means for guiding the gas-borne dispersion of solute particles to a target human or animal.

17. A hand-held apparatus as defined by claim 16, wherein the second chamber contains a removable support matrix which holds the physiologically active solute.

18. A hand-held apparatus for delivering a physiologically active compound to a target human or animal, comprising (a) a first chamber containing a supercritical fluid solution comprising a supercritical fluid solvent and a physiologically active solute; (b) means for rapidly expanding the solution into a region in which the temperature and pressure of the solvent are below a critical temperature and a critical pressure, respectively, of the solvent to evaporate the solvent and form a gas-borne dispersion of solute particles; (c) a second chamber containing a pressurized ballast fluid; (d) impermeable pressure sensitive barrier means arranged between the first chamber and the second chamber, which pressure sensitive barrier means allows the pressure of the ballast fluid to maintain the supercritical condition of the solution as the solution passes through the rapid expansion means; and (e) means for guiding the gas-borne dispersion of solute particles to a target human or animal.

19. A hand-held apparatus as defined by claim 18, wherein the pressure sensitive barrier means comprises a sliding piston.

20. A hand-held apparatus as defined by claim 18, wherein the pressure sensitive barrier means comprises a flexible wall.

21. A hand-held apparatus for delivering a physiologically active compound to a target human or animal, comprising (a) a first chamber containing (i) a supercritical fluid solution comprising a supercritical fluid solvent and a physiologically active solute and (ii) a pressurized ballast fluid, the difference in the density of the supercritical fluid solution and the density of the ballast fluid being sufficiently large that the supercritical fluid solution and the ballast fluid are separated from one another; (b) means for rapidly expanding the solution into a region in which the temperature and pressure of the solvent are below a critical temperature and a critical pressure, respectively, of the solvent to evaporate the solvent and form a gas-borne dispersion of solute particles; and (c) means for guiding the gas-borne dispersion of solute particles to a target human or animal.

* * * * *